US00PP28962P3

(12) United States Plant Patent
Stemkens

(10) Patent No.: US PP28,962 P3
(45) Date of Patent: Feb. 13, 2018

(54) ***AUBRIETA* PLANT NAMED 'ABRZ0006'**

(50) Latin Name: *Aubrieta hybrida*
Varietal Denomination: ABRZ0006

(71) Applicant: SYNGENTA PARTICIPATIONS AG, Basel (CH)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 59 days.

(21) Appl. No.: 14/999,546

(22) Filed: May 23, 2016

(65) Prior Publication Data

US 2017/0135261 P1 May 11, 2017

Related U.S. Application Data

(60) Provisional application No. 62/252,740, filed on Nov. 9, 2015.

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Keith O Robinson
(74) *Attorney, Agent, or Firm* — Dale Skalla

(57) ABSTRACT

A new *Aubrieta* plant named 'ABRZ0006' particularly distinguished by its lilac blue flowers, a compact and mounding habit with strong vigor, and a good winter hardiness.

1 Drawing Sheet

Latin name of the genus and species of the plant claimed: *Aubrieta hybrida.*

Varietal denomination: 'ABRZ0006'.

BACKGROUND OF THE NEW PLANT

The present invention comprises a new *Aubrieta*, botanically known as *Aubrieta hybrida* and hereinafter referred to by the variety name 'ABRZ0006'.

'ABRZ0006' is a product of a planned breeding program. The new cultivar 'ABRZ0006' has lilac blue flowers, a compact and mounding habit with strong vigor, and is very winter hardy.

'ABRZ0006' originates from a hybridization in a controlled breeding program in a greenhouse in Enkhuizen, The Netherlands. The female parent was an unpatented, proprietary plant identified as 'F1044-51' with magenta flowers and more branching compared to 'ABRZ0006'.

The male parent of 'ABRZ0006' was an unpatented, proprietary plant identified as 'H2669-52' with a purple flower color, less branching and later flowering compared to 'ABRZ0006'. The resultant seed was sown in August 2008 in a greenhouse, in Enkhuizen, The Netherlands.

'ABRZ0006' was selected as one flowering plant within the progeny of the stated cross in March 2009 in a greenhouse in Enkhuizen, The Netherlands.

The first act of asexual reproduction of 'ABRZ0006' was accomplished when vegetative cuttings were propagated from the initial selection in June 2009 in a greenhouse in Enkhuizen, The Netherlands.

BRIEF SUMMARY OF INVENTION

Horticultural examination of plants grown from cuttings of the plant initiated in August 2009 in Enkhuizen, The Netherlands, and continuing thereafter, has demonstrated that the combination of characteristics as herein disclosed for 'ABRZ0006' are firmly fixed and are retained through successive generations of asexual reproduction.

'ABRZ0006' has not been observed under all possible environmental conditions. The phenotype may vary significantly with variations in environment such as temperature, light intensity and day length.

A Plant Breeder's Right for this cultivar was applied for in the European Union on May 27, 2015 and assigned application no. 2015/1076. 'ABRZ0006' has not been made publicly available more than one year prior to the filing of this application.

The following traits have been repeatedly observed and are determined to be basic characteristics of the new variety. The combination of these characteristics distinguishes this *Aubrieta* as a new and distinct variety.

BRIEF DESCRIPTION OF THE PHOTOGRAPHS

The accompanying photographic drawing shows typical flower and foliage characteristics of 'ABRZ0006' with colors being as true as possible with an illustration of this type.

The photographic drawing shows in FIG. 1 a close-up of the flowers.

DETAILED BOTANICAL DESCRIPTION

The plant descriptions and measurements were taken in Enkhuizen, The Netherlands under natural light in March 2015. These plants were approximately 22 weeks old and were growing in 13 cm pots in shade-house trials.

The plants used for the photographs were about 22 weeks old grown in Enkhuizen, The Netherlands and taken in March 2015.

Color Chart used: Royal Horticultural Society Colour Chart (R.H.S.) 2001

TABLE 1

DIFFERENCES BETWEEN THE NEW VARIETY 'ABRZ0006' AND A SIMILAR VARIETY

| | 'ABRZ0006' | 'Axcent Lilac' (Not patented) |
|---|---|---|
| Leaf size: | Smaller | Bigger |
| Earliness: | 3 weeks earlier | Later |
| Flower size: | Bigger | Smaller |

Plant:

*Form, growth and habit.*—Mounding, spreading.

*Plant height.*—9 cm.

*Plant height (inflorescence included).*—12 cm.

*Plant width.*—20 cm.

Roots:

*Number of days to initiate roots.*—About 6 days at 18 degrees C.

*Number of days to produce a rooted cutting.*—2.5 weeks at 18 degrees C.

*Type.*—Fine, fibrous, free branching.

*Color.*—RHS N155B but whiter.

Foliage:

*Arrangement.*—Alternate.

*Immature, leaf color.*—Upper surface: RHS 137B. Lower surface: RHS 144A.

*Mature, leaf color.*—Upper surface: RHS 137B. Lower surface: RHS 144A.

*Length.*—3-4 cm.

*Width.*—1.5-2.2 cm.

*Shape.*—Oblanceolate.

*Base shape.*—Attenuate.

*Apex shape.*—Acute.

*Margin.*—Slightly dentate.

*Texture.*—Pilose.

*Color of veins.*—Upper surface: RHS 144C. Lower surface: RHS 144A, just shinier than the rest of the leave.

*Pattern of veining.*—Pinnate.

*Petioles color.*—RHS 144C.

*Petioles length.*—2 cm.

*Diameter of petiole.*—0.4 cm.

*Texture.*—Hirsute.

Stem:

*Color of stem.*—RHS 145C.

*Length of stem.*—6-9 cm.

*Diameter.*—0.4 cm.

*Length of internodes.*—0.5-1 cm.

*Texture.*—Pilose.

*Color of peduncle.*—RHS 144B.

*Length of peduncle.*—4-7 cm.

*Peduncle diameter.*—0.3 cm.

*Texture.*—Pilose.

*Color of pedicel.*—RHS 144B.

*Length of pedicel.*—1.5-3 cm.

*Diameter of pedicel.*—0.1-0.2 cm.

*Texture.*—Pubescent.

Inflorescence:

*Type.*—Flowers Single, cruciform, composed of 4 petals, flowers held above the plant.

*Number of flowers per inflorescence.*—10-15.

*Quantity of inflorescences per plant.*—30.

*Lastingness of individual blooms on the plant.*—15 days.

*Fragrance.*—None.

Bud (just before opening/showing color):

*Color.*—RHS 144C to RHS 137C.

*Length.*—1.2 cm.

*Width.*—0.5 cm.

*Shape.*—Oblong.

Corolla:

*Immature inflorescence.*—Diameter: 2 cm. Color petals, upper surface: Very deep RHS N78A. Color petals, lower surface: RHS N78B.

*Mature inflorescence.*—Form: Rounded square. Flower diameter: 3-3.2 cm. Depth of flower: 2 cm.

*Number of petals.*—4.

*Petal shape.*—Flower seems semi-double, 2 to 3 petals are deeply separated, sometimes from the petal base.

*Color upper petals.*—Upper surface: RHS N78A. Lower surface: RHS N78B.

*Length of petals.*—2.5 cm.

*Width of petals.*—1.3 cm.

*Petal shape.*—Spathulate, 2-3 petals are deeply separated, sometimes from the petal base.

*Apex shape.*—Rounded.

*Margin.*—Entire.

*Corolla texture.*—Inside: Glabrous, papillose. Outside: Glabrous, papillose.

*Corolla tube color.*—Inside: RHS 151D. Outside: RHS 151D.

*Duration of flowering.*—Continuous flowering throughout the Spring until beginning of June.

Calyx:

*Number of sepals.*—4.

*Color of sepals.*—RHS 144B to C at the top turning to RHS 187A towards the base.

*Length of sepals.*—1.2-1.4 cm.

*Width of sepals.*—0.3 cm.

*Sepal shape.*—2 types: 2 are oblanceolate, situated on the opposite of each other, and 2 are oblong, also on the opposite of each other. The particularity is that the 2 oblong sepals are swollen at the base on mature flowers.

*Apex shape.*—For the oblanceolate shaped sepals: Obtuse. For the oblong ones: Acute.

*Margins.*—Entire.

*Texture.*—Inner/upper surface: Smooth. Outer/lower surface: Stellate hairs.

*Base.*—Fused.

Reproductive organs:

*Gynoecium.*—Pistil quantity: 1. Length: 1.6 cm. Style color: RHS 144A. Style length: 0.5 cm. Stigma color: RHS N144A. Stigma shape: Disc shaped. Ovary color: RHS 144D. Ovary size: 0.5 cm.

*Androecium.*—Number of stamens: 6. Length of stamens: 1 cm. Anther color: RHS 145C. Anther length: 0.2 cm. Anther shape: Ovate. Length filaments: 1.2 cm. Color of filaments: RHS 145C. Pollen amount: Moderate. Color of pollen: RHS 151D.

*Fertility/seed set.*—Neither seed nor fruit production has been observed.

*Disease/pest resistance.*—Resistance to pathogens and pests common to *Aubrieta* has not been observed.

*Drought tolerance and cold tolerance.*—Hardy perennial. Tolerates high temperature to at least 30 degrees C. Tolerates low temperatures to degrees minus 20 C. No specific drought tolerance has not been observed.

What is claimed is:

1. A new and distinct variety of *Aubrieta* plant named 'ABRZ0006' substantially as illustrated and described herein.

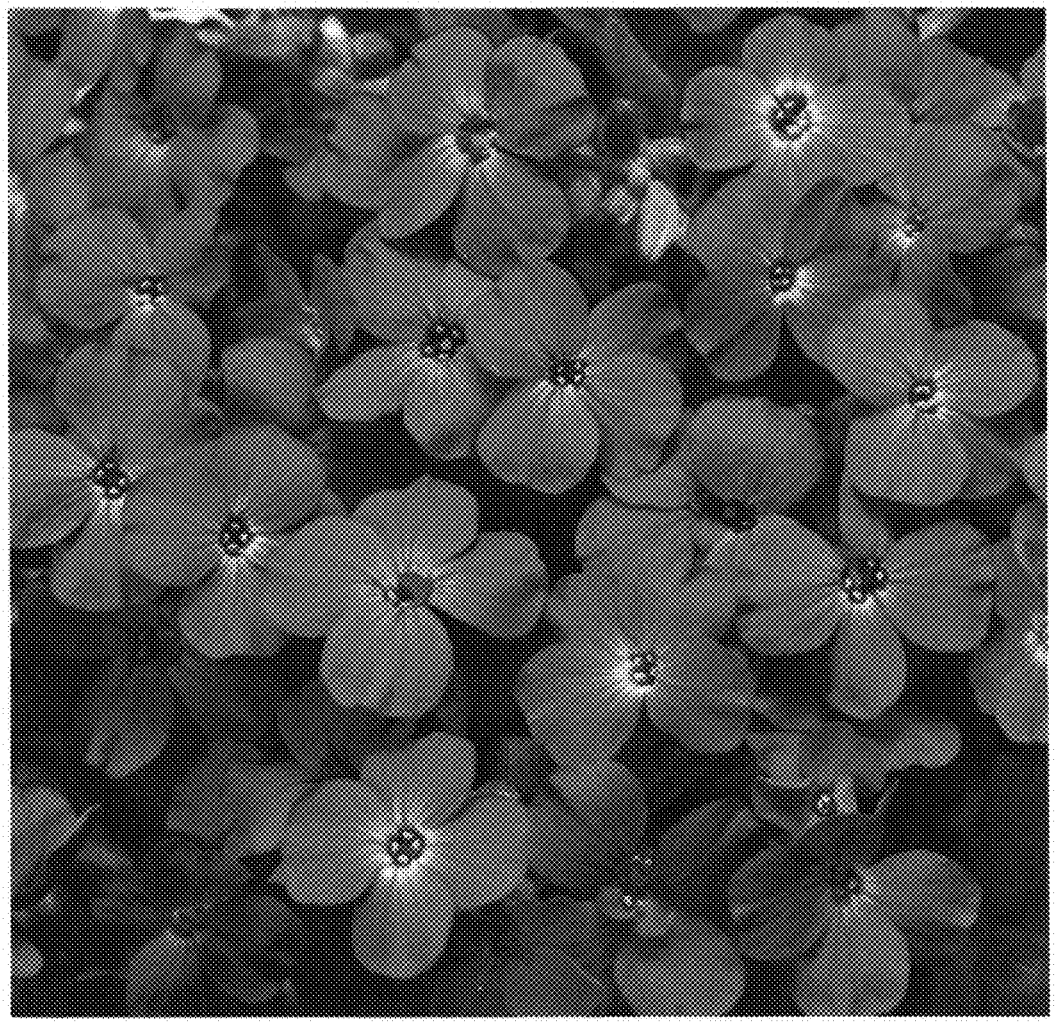

* * * * *